(12) United States Patent
Niemelä et al.

(10) Patent No.: US 8,786,836 B2
(45) Date of Patent: Jul. 22, 2014

(54) MEASURING INSTRUMENT AND METHOD FOR DETERMINATION OF THE PROPERTIES OF AN ITEM AND ITS SURFACE

(75) Inventors: Karri Niemelä, Oulu (FI); Heimo Keränen, Oulu (FI)

(73) Assignee: Focalspec Oy, Oulu (FI)

( * ) Notice: Subject to any disclaimer, the term of this patent is extended or adjusted under 35 U.S.C. 154(b) by 184 days.

(21) Appl. No.: 13/500,073

(22) PCT Filed: Oct. 7, 2010

(86) PCT No.: PCT/FI2010/050778
§ 371 (c)(1),
(2), (4) Date: Apr. 4, 2012

(87) PCT Pub. No.: WO2011/042606
PCT Pub. Date: Apr. 14, 2011

(65) Prior Publication Data
US 2012/0206710 A1    Aug. 16, 2012

(30) Foreign Application Priority Data
Oct. 8, 2009 (FI) .................................... 20096035

(51) Int. Cl.
*G01C 3/08* (2006.01)

(52) U.S. Cl.
USPC .......... 356/4.01; 356/3.01; 356/4.1; 356/5.01

(58) Field of Classification Search
USPC ............ 356/3.01–3.15, 4.01–4.1, 5.01–5.15, 356/6–22, 28, 28.5
See application file for complete search history.

(56) References Cited

U.S. PATENT DOCUMENTS

2008/0130013 A1* 6/2008 Stautmeister et al. ........ 356/609

FOREIGN PATENT DOCUMENTS

| FR | 2848664 | 11/2002 | |
| FR | 2848664 | * 12/2002 | .............. G01D 5/26 |
| WO | 2008/046966 | 4/2008 | |

OTHER PUBLICATIONS

Erez Hasman et al., "Color-coded optical profilometry with >106 resolved depth steps", Applied Optics, Apr. 1, 2001, pp. 1609-1616.

*Primary Examiner* — Luke Ratcliffe
(74) *Attorney, Agent, or Firm* — Mark M. Friedman (57) ABSTRACT

A measurement device for the determination of the characteristics of the object's surface by means of the optical radiation, wherein a measurement device comprises an optical radiation source and a detector to receive the radiation reflected from the surface being measured. In addition, a measurement device comprises an emitted optical radiation processing unit, which is adjusted to split optical radiation emitted by an optical source into separate wavelengths and to direct said separate wavelengths to the object being measured in a direction, that differs from the normal of the surface being measured so, that at least the shortest and the longest wavelengths of said wavelengths are focused on different halves and different heights of the measured object's surface, in the direction of the normal of the surface being measured. In addition, a measurement device comprises a reflected optical radiation processing unit, which is adjusted to receive an optical radiation reflected from the measured object at least in the direction of a specular reflection, which differs from the normal of the surface being measured, and to direct received optical radiation to said detector. Still further, the measurement device is adjusted to analyze an electric signal produced by the detector and proportional to the intensity of the radiation focused thereto, and to further determine a surface gloss (gloss degree) and/or thickness characteristic property of the measured object, based on the intensity of its wavelength, the focus point of which was located on the measured surface, and which wavelength was the strongest reflected from that point to the detector in the specular geometry.

13 Claims, 4 Drawing Sheets

MEASURING INSTRUMENT AND METHOD FOR DETERMINATION OF THE PROPERTIES OF AN ITEM AND ITS SURFACE

TECHNICAL FIELD OF THE INVENTION

The invention relates to measuring instruments and methods, in particular to those, directed to measure surface properties of an item, such as gloss, refraction index and/or thickness.

BACKGROUND OF INVENTION

Control over properties of the surface of an item, such as, for example, monitoring quality of the paper, metal and various film's surfaces, as well as control over thickness of the surface, is a key part during, for instance, process control and product quality control. One well-known and commonly utilized parameter for the surface quality characterization is a gloss degree. Optical measurement of the surface gloss degree is commonly used and well documented, for example, in ISO-standard 2813 "Paints and Varnishes—Determination of specular gloss if non-metallic paint films at 20° 60° and 80°". At the time present, for example in steel industry, gloss degree is determined mainly in the laboratories in so called offline-mode, by using a separate point-like sensor. Determination of gloss parameters by using the point-like sensor is slow, and does not allow real-time tuning of the process, for example.

Also other systems for determining gloss of the surface are known from prior art. For example, in WO 01/20308 a solution is disclosed, wherein a light emitted by a light source is directed towards the measured surface so, that the light reflects from the surface to a detector. The detector, in turn, measures the intensity of the reflected light and determines a gloss of the surface on the basis of the intensity of the reflected light. In solution disclosed, a sensitivity of the detector can be changed. An instrument in turn, can be calibrated by a programmable constant value so that certain gloss units are given as the measurement result.

In addition, in EP 1 407 248 B1 a solution for surface gloss measurement is disclosed, wherein a light, emitted by a light source is collimated and split to two different beams, from which the first beam is directed via the first mirror towards the measured surface, and the second beam is directed through a prism to the first mirror, and, further, to the second mirror. The first beam is reflected from the measured surface to the second mirror and further from there to the detector. The second beam reflects, through the prism, to the second detector. In addition, a solution implies the use of a third detector in order to form a reference signal.

Still, as a prior art for measuring surface properties the document FI 119259 B is known, in which a solution is disclosed, wherein a light, emitted towards the surface, is decentralized, forming a spectrum so, that different wavelengths of the spectrum focus on different heights in the direction of the normal of the surface being measured. In the solution disclosed, on the basis of signal from the detector, an emission wavelength is determined at which the intensity of the optical radiation is the highest, and the location of the surface is determined based on the measured wavelength. In addition, according to the solution, the thickness of an object is determinable by measuring the location of upper- and lower surface planes.

However, known solutions have some drawbacks. For example, if the surface being measured is moving or trembling, an intensity of light, reflected from the surface, varies, regardless of a fact that gloss degree of the surface would be constant. It could also happen so, that focused light from the radiation source would not hit the proper spot on the surface being measured thereby the intensity of the reflected light could change. The reason for these drawbacks may be, for instance, that the distance and/or angle of trembling surface with respect to the detector are changing. Also the shape of the surface may vary, thereby affecting the intensity of reflected radiation, regardless of fact, that a gloss degree would stay unchanged. Therefore solutions disclosed in prior art do not necessarily lead to reliable results during measurements of moving surface properties, for example.

SUMMARY OF INVENTION

It is an object of a present invention to implement such a solution, that previously mentioned drawbacks of a prior art could be diminished. In particular, the invention is implied to solve, how to monitor properties, such as gloss, refraction index and/or thickness, of moving or trembling surfaces.

The objective of the invention is met by the features disclosed in the independent patent claims.

The measuring device according to the present invention is characterized by features disclosed in characterizing part of the independent claim describing the measuring instrument.

The measurement method according to the present invention is characterized by features disclosed in characterizing part of the independent claim describing the measurement method.

The computer program product according to the present invention is characterized by features disclosed in characterizing part of the independent claim describing the computer program.

According to an embodiment of the invention, properties of an object and/or its surface are determined by means of optical radiation so that optical radiation is emitted towards the surface being measured by means of at least one source of optical radiation, and an intensity of radiation reflected from the surface is monitored by at least one detector, which generates an electrical signal proportional to the radiation intensity. According to the invention, the radiation, such as white or other preferably continuous spectral light, emitted by an optical source, is split into different wavelengths. Wavelengths are then focused on an object being measured in a direction, that differs from the normal of the surface being measured, so that at least the shortest and the longest wavelengths of said wavelengths would focus on different halves and on different heights of the measured object's surface, in the direction of the normal of the surface being measured.

For example, red spectrum wavelengths may be focused on the upper surface plane and blue spectrum wavelengths—on the lower surface plane of the object being measured.

In accordance with the invention one can always be assured that at least some of the wavelengths located between the longest and the shortest of a spectrum will focus substantially on the surface of an object being measured, even if the shape of the surface and, therefore, location and distance in regards to the detector, would not be constant, but would change because of moving or trembling of the surface. Still, in accordance with the invention, a strongest intensity value, corresponding to an optical ray reflected from a surface of an object, can always be defined, because the intensity values of rays focused onto elsewhere are essentially smaller that those, that are reflected from the surface of an object. In addition, according to the invention, a wavelength of an optical ray generating the strongest intensity value can be determined.

Surface gloss affects an intensity of an optical ray reflected from the surface so that the glossier a surface is, the higher is the intensity value of a ray, reflected from the surface, and, accordingly, the blurrier the surface is, the less its shines and therefore the weaker is the intensity of a ray, reflected from the surface. In addition, also optical rays, emitted from different optical sources, may have differing characteristic intensities; and, whereby, according to an embodiment of the invention, characteristic intensity for each wavelength or, at least for a wavelength band, comprising of some wavelengths, is known. According to some embodiment of the invention, a gloss degree of a surface may be determined by defining the highest intensity value of light reflected to the detector (corresponding to the ray focused on the surface and reflected from there) and the wavelength of said ray, and by further comparing, for example, to characteristic intensity values of said wavelengths.

In accordance to the invention, an optical radiation, reflected from the measured surface substantially to the direction of the specular reflection, is captured by the detector, wherein the direction of the specular reflection differs from the direction of the normal of a surface being measured. Reflected radiation represents substantially that wavelength, focus point of which hit the surface of an object. From the electric signal generated by the detector, which signal is proportional to the radiation intensity, a gloss degree is then determined, which characterizes the gloss of the object's surface based on the intensity value of that wavelength, the focus point of which was located on the surface being measured and the wavelength of which was the strongest reflected from that point to the detector in the specular geometry.

Detector is preferably assembled so that with it can differentiate intensity values of optical radiation directed to it and at least certain wavelength bands. Intensity values can be determined, for example, by means of the voltage generated by the detector and the wavelength can be determined based on the data which spot of the detector (for example, a multi-channel row detector) is hit by an optical ray corresponding to particular wavelength. Detector may be, for example, a detector based on CCD or CMOS-technique.

According to the one embodiment of the invention, also two separate detectors can be used as a monitoring device for optical radiation reflected from the surface so, that the light, reflected from the surface is split for two different detectors by means of an optical filter whose penetration capability changes, for examples, increases or decreases, as a function of a wavelength. In this case, at least two different wavelengths or wavelength bands can be separated for two different detectors and focus of the peak intensity is proportional to the ratio:

$$\lambda_p \sim \frac{S_1 - S_2}{S_1 + S_2}$$

wherein $S_1$ and $S_2$ are signals from detectors 1 and 2.

A gloss degree $G_0$ characterizing the gloss of an object's surface being measured can be determined from the following equation:

$$G_0 = \frac{G_B - G_A}{\varphi_B - \varphi_A} \varphi_0 + \frac{G_A \varphi_B - G_B \varphi_A}{\varphi_B - \varphi_A}$$

wherein $\varphi_0$ is an intensity measured by a detector (pixel grayscale value); $G_A$ and $G_B$ are the gloss degree of first and the second references; and $\varphi_A$ and $\varphi_B$ are intensity values corresponding to latter.

According to the one embodiment of the invention, by an arrangement of the present invention, in addition to the gloss degree, the location of the surface of an object being measured can be determined in connection with the measurement of a gloss degree. In this case a distance to, or a location of focus points for wavelengths are known e.g. in relation to some reference point, for example to a downright distance measured from the top of the detector. According to the invention, the location of the surface of a measured object is then defined by determining the wavelength at which the intensity value of a reflected light is the strongest. When the wavelength is determined, and a distance to focus point at each wavelength is known in relation to reference point, then the surface location can be determined.

According to some example, e.g. visible to human eye wavelengths of 450-650 nm can be spread to, for instance, 1 mm z-zone, i.e. relative to the direction of the surface's normal. When using as measurement setup, for example, a charge coupled device (CCD) with 1000×1000 pixels array, correspond 1 pixel of 0.2 nm, and when mentioned above 200 nm are spread to the area of 1000 pixels, and the pixel resolution is 1 micrometer for a 1 mm z-zone. Then, by defining a location of an optical radiation directed to the detector, for example, by peak intensity calculation, it is possible with certain solutions to reach even a 0.1 pixel precision, which corresponds to the 0.1 µm height precision relative to the direction of the surface's normal In other words, an object's surface location is determined by using a wavelength of strongest intensity value reflected from the surface, by comparing it to a distance of a focus point for a said wavelength from some reference point. According to the invention, a location of a surface being measured may be defined, by using a setup mentioned above, even with 0.1 µm precision rate at some reference points. It should be however pointed out that those numerical values mentioned above are only exemplary and are implied to give an average idea of an invention to those, skilled in art; but these values are not implied to limit the invention in any way and the invention may be adapted for utilization of other wavelengths, much shorter or longer, such as, for example, ultraviolet and infrared light.

According to some embodiment of the invention, in addition to determination of gloss degree and surface location, the invention can also be applied for the thickness measurement of an object, wherein the object is at least partly transparent for an optical radiation. An object may be, for example, a film comprising at least two substantially parallel to each other surfaces, the upper and the lower. According to the embodiment, e.g. at least the shortest and the longest wavelengths of the spectrum of the spread wavelengths may be focused so, that the upper- and the lower surfaces of an object remain in between the focus points for said wavelengths (for example between the blue and red ends of the spectrum).

According to the certain embodiment of the invention, a thickness of an object can be then determined so, that the wavelengths reflected from both surfaces, are received. For a very thin object, such as a film, the wavelengths reflected from the upper- and lower surface planes, are so close that they could not necessarily be separated as two different intensity peaks (depends on the resolution of the detector), but instead they are detected as a single broad peak. In this case, the thickness of an object can be determined by means of the function of Full Width at Half Maximum (FWHM) of an intensity peak or signal, for example, by calculating a signal variance.

Signal has a so called "characteristic width", which is characteristic for optical measurements. The characteristic width is directly proportional to that, into how broad z-zone the spectrum is spread, as well as directly proportional to that, how wide is the entrance slit of optics, and also inversely proportional to the illumination numerical aperture (NA). Characteristic width of a signal can be measured by determination, for instance, of a Full Width at Half Maximum of a signal reflected from the perfectly shiny reflective surface (such as optimum mirror). When the optical ray penetrates the transparent film also into the film, in principle, two signals, from which the one is caused by the light reflected from the upper surface plane and the other—by the light reflected from the lower surface plane, are obtained to the detector. When the film is thin enough, intensity peaks, caused by these rays, are get mixed with each other, which makes a Full Width at Half Maximum value of an emerged signal to broaden up, wherein a FWHM value of a signal is directly proportional to the thickness of film.

According to another embodiment of the invention, if an object is thick enough or, alternatively, a resolution of a detector is sufficient, then the high intensity peaks reflected from upper and lower surfaces of an object can be separated as individuals, whereby also corresponding to said intensities wavelengths and, further, by means of said wavelengths the locations of an object's surface can be determined, from which the wavelengths are reflected. Based on the locations of the surfaces a thickness of an object can be determined.

According to the other embodiment of the invention, in particular in case of using a detector with sufficient resolution, also the thickness of the multilayered object and the distance in between the layers of the multilayered object can be defined, wherein the multilayered object is totally or at least partly transparent to the radiated light. In that case, the radiation spectrum of the source of the optical radiation is divided so, that a whole object, and, therefore, all its layers remain in between the extremes of the spectrum, like in previous embodiments. Then it is expected that at least one of the wavelengths is focused on the surface of each of an object's layers and is reflected from there to the detector. Thus, the thickness of the first layer of the object can be determined by means of two first intensity peaks according to the previous embodiment of the invention, the thickness of the second layer—by means of the third and the forth intensity peaks and so on. Accordingly, the gaps between layers can be measured so that for example the first gap can be determined by means of the second and the third intensity peaks, or, in other words, by means of the wavelengths reflected from the lower surface plane of the first layer and the upper surface plane of the second layer.

According to an embodiment of the invention, a thickness of different layers can in appropriate circumstances be determined using a detector with even coarser resolution based on broadening of intensity peaks, as disclosed previously. In this case, however, the distance between layers should be such, that a broadening of the intensity peak generated by the first layer does not interfere too much with the radiation reflected from the second layer and the intensity peak generated by it.

Moreover, according the certain embodiment of the invention, a present idea can be applied, in addition to measuring a gloss degree of a object's surface, to the determination of an object's surface profile when the object being measured and a measurement device are moved in relation to each other. By applying previously disclosed embodiments, more than one surface's profile of an object, which object is at least partly transparent, can be also determined, in condition that either a distance between surface planes is sufficient or, alternatively, a resolution of the used detector is high enough.

According to still another embodiment of the invention, several invention-related measurement arrangements can be arranged around an object being measured, for example the first measurement arrangement—above the upper surface of the object, and the second measurement arrangement—below the lower surface of an object, in which case the first measurement arrangement may determine e.g. a location of the first (upper) surface and the second measurement arrangement—a location of the second (lower) surface in relation to some reference point. In such a case, a thickness of an object may be calculated based on the location of the surfaces. Said embodiment may also be adapted for an object's profile determination, in other words not only for a surface's profile determination, by combining the measurement data from the first and the second measurement arrangement in appropriate way.

Embodiments of the invention are therefore based on a chromatic aberration and a spectral illumination of a measured object, or in other words, on a phenomenon, wherein different wavelengths of light are made to refract and also to focus onto different points in space. For example, the shortest wavelengths of the spectrum refract in a greater degree in a lens comparing to the longest wavelengths of the spectrum. Light refraction depends on refractive index of a lens or other refractive object. The refractive index depends on the Other hand on a light's wavelength; from which follows that the different wavelengths refract at different angles, in which case the chromatic aberration is observed. Generally speaking, blue light refracts more that red.

The invention offers significant advantages in comparison to solutions known from prior art, namely, measuring the surface's gloss degree regardless of movement or vibration of a measured surface; or change in a surface angle. In addition, the invention enables the measuring the gloss degree and the thickness and/or surface's profile at the same time and using the same probe, which was previously not possible. The invention is not limited to the spot measurements of the gloss degree, but enables also measuring the gloss profile, i.e. so-called image-based gloss measurement.

The invention can be applied very broadly, for example in fields of paper, steel, and plastics industries, where the monitoring of the surface's gloss parameters is an essential part of the process- and the product quality control. A particular advantage is the fact that gloss degree and thickness of an object can be measured in real time, in connection, for example, with the production process, with no additional need in performing time-consuming laboratory measurements. In addition, the results obtained by the invention, can be used for real-time tuning of the production line instruments, thereby the quality of an end-product can be affected directly, not after measurements performed apart from the production process. It has a clear impact both on the production process quality assurance and the poor quality products minimization and the speed for introducing required measures, since the control parameters of the product manufacturing can be adjusted in real-time.

Some preferred embodiments of the invention are disclosed in claims.

BRIEF DESCRIPTION OF THE DRAWINGS

Next, preferred embodiments of the invention will be described in more detail with reference to the following drawings, wherein.

DETAILED DESCRIPTION OF THE INVENTION

Figure 1:
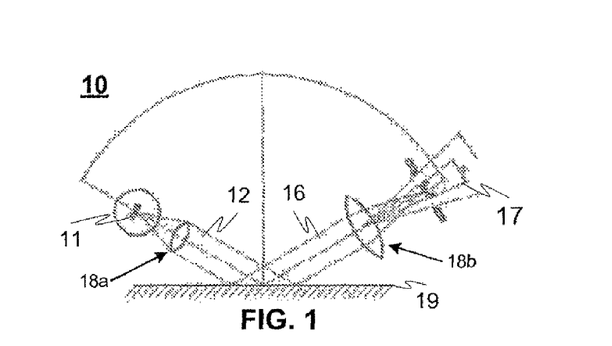
FIG. 1 illustrates gloss measurement geometry according to a certain ISO standard.

FIG. 1 illustrates a gloss measurement geometry 10, according to the gloss standard ISO 2813, wherein an optical beam 12; generated by an optical source 11, is directed by a convergence device 18a, for example a lens, to the surface being measured 19. Optical ray is reflected from the surface 19 to the direction of the specular geometry 16, where it is collected by a convergence device 18b, e.g. a lens, to the optical radiation detector 17. Detector 17 measures an intensity of the reflected optical ray 16 and determines the gloss degree of a surface being measured 19, on the basis of the intensity of the ray 16.

Figure 2A:
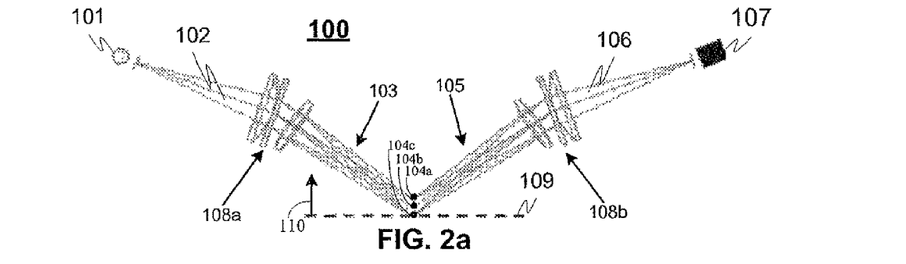
FIG. 2a illustrates an exemplary measurement arrangement according to an embodiment of the present invention.

FIG. 2a illustrates an exemplary measurement arrangement 100 according to a certain embodiment of the present invention, wherein a system comprises an optical radiation source 101, for emitting an optical radiation 102, such as white or other reasonably continuous spectral light, towards the optical radiation processing unit 108a. Optical radiation processing unit 108a is adjusted to split a light emitted to it into a spectrum 103 so, that for example the shortest wavelength (blue end) refracts the most, thereby its focus point, regarding to the direction of a normal of a measured surface 110, constitutes, for instance, point 104a; a focus point for a slightly longer wavelength constitutes point 104b; and thereby the longest wavelength (red) refracts the least, in which case its focus point, regarding to the direction of a normal of a measured surface 110, constitutes point 104c.

An optical radiation 105, reflected from the measured surface 109 to the specular geometry, is collected by the processing unit 108b and is further directed 106 to the optical radiation detection unit 107, which, in turn, can be adjusted to produce, as an output, e.g. an electric signal proportional to the intensity of the optical ray hit thereto. Detector 107 can also determine the wavelength of said intensity in a way disclosed in the present document.

A measurement arrangement comprises also means 111 for determining the gloss degree of a surface of the measured object on the basis of an intensity of a reflected ray. The means may, for example, know beforehand the characteristic intensity of the wavelength of the corresponding ray, and regarding to it, how different surfaces, surface coatings, used geometries and/or surface gloss degree affect the intensity. Based on the mentioned above data, measurement arrangement is preferably adjusted to determine gloss degree of the surface of the object.

Incidence angles of optical radiation in regards to the measured surface, for example, to its normal, may change from few degrees to tens of degrees depending on the measurement scenario. An arrangement disclosed, from the other hand, enables exploitation of sufficiently large incidence and, accordingly, departure angles, for instance, equal to few tens degrees, in a measurement. For example, for a gloss degree measurement many different angles are commonly used, also, said large angles. Measurement geometry is preferably adjustable.

Figure 2B:
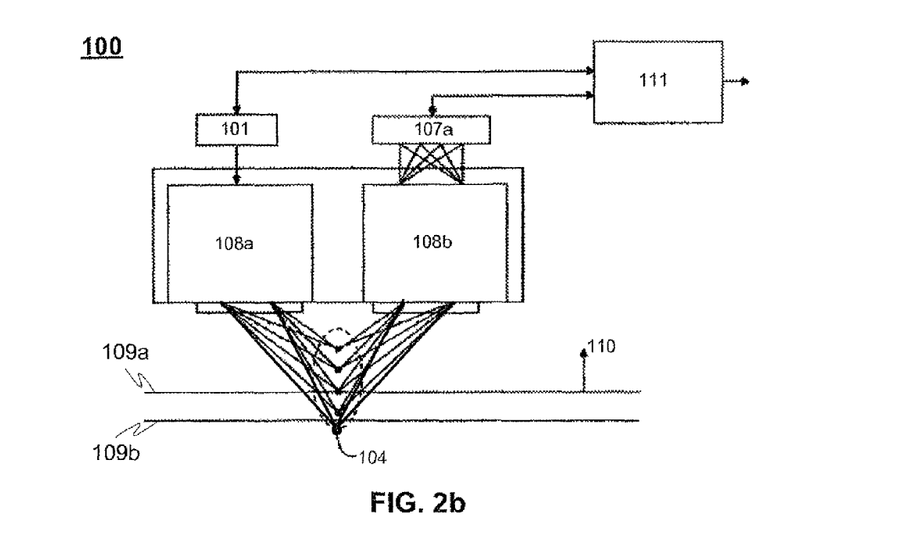
FIG. 2b illustrates an exemplary measurement device according to an embodiment of the present invention.

FIG. 2b illustrates one exemplary measurement device 100 according to a certain embodiment of the present invention, wherein an optical radiation, produced by an optical source 101, is split into spectrum and is focused by the processing unit 108a in such a way, that at least part of the wavelengths focuses 104 above the surface 109a of the measured object which is closer to the measurement device 100, and part— below the surface 109b.

In case depicted by FIG. 2b, a measured surface can be, for example, a material substantially transparent to the optical radiation, wherein, according to one of the preferred measurement principle of the invention, at least one wavelength focuses substantially to the point of the upper surface 109a of the object being reflected from there towards the processing unit 108b, and at least one another wavelength penetrates to a transparent layer located in between surfaces 109a and 109b and focuses to the lower surface 109b being reflected from there towards the processing unit 108b.

By means of an optical radiation processing unit 108b different wavelengths can be directed to the distinct points of the detector 107a. Detector 107a is preferably adjusted to detect the strongest intensities, which are due to, in case depicted on FIG. 2b, the rays reflected from the surfaces 109a and 109b. On the basis of two strongest intensities it can be determined which rays hit the surfaces 109a and 109b, and by means of these rays the corresponding wavelengths can be defined on the basis of to which spots on the detector 107a said rays hit. Accordingly, based on wavelengths, the distance of surfaces 109a and 109b to a certain reference point can be determined, since the location of a focus point or a distance of said wavelengths with regards to a reference point is known or at least, can be calculated mathematically. Furthermore, based on the knowledge on surface locations, a middle layer, remaining in between surfaces, can be determined, i.e. a thickness of an object. In case of the rays reflected from the surfaces 109a, 109b of thin objects, such as, for example transparent films, are focused so close to each other in the detector 107a, that signals get mixed to each other, thereby film's thickness can be determined from a Full Width at Half Maximum value of signal, as described previously in this document, for example.

Figure 2C:
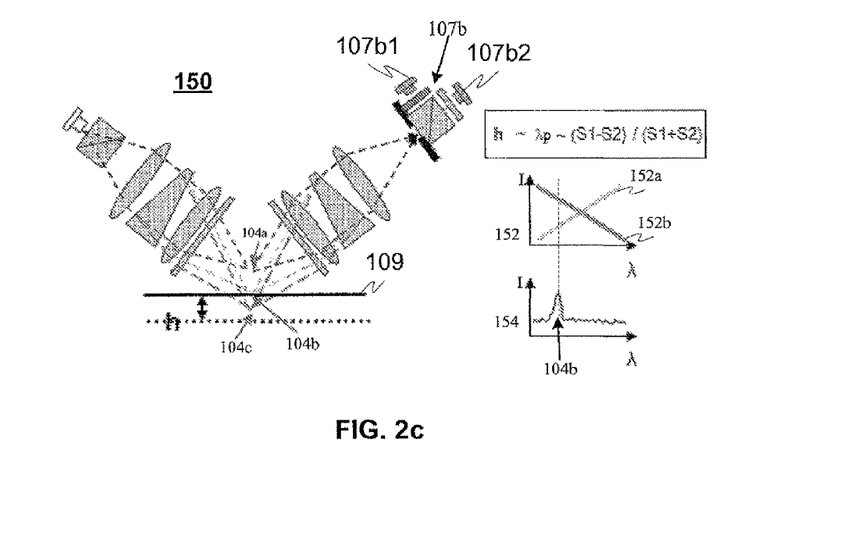
FIG. 2c illustrates the other exemplary measurement device according to an embodiment of the present invention.

FIG. 2c illustrates another exemplary measurement device 150 according to an embodiment of the present invention, which measurement principle is otherwise the same as for the device 100 depicted in FIG. 2b, except that as an optical radiation detection unit 107b of the instrument 150 two separate detectors 107b1 and 107b2 are used so, that the light, reflected from the surface, is split for two separate detectors by means of e.g. semi-transparent mirror and by using e.g. an optical filter, which penetration changes (for example, increases or decreases) as a linear function of a wavelength, such as depicted on diagram 152, wherein the filtration of the ray arrived e.g. to the detector 107b1 is shown by the curve 152a as a function of the wavelength, and the filtration of the ray arrived to the detector 107b2 is shown by the curve 152b as a function of the wavelength. This way at least two different wavelengths or wavelength bands can be separated for two different detectors.

When detected by both detectors at each of the wavelengths optical power (or intensity) is summed together, and divided by the difference in detected optical power, in this way from the relative intensity in the place of the greatest relative intensity such wavelength is generated, which is reflected from the surface of a measured object. Then the focus of the peak intensity is proportional to the ratio:

$$h \sim \lambda_p \sim \frac{S_1 - S_2}{S_1 + S_2}$$

wherein h is a surface distance from some reference point, $\lambda_p$ is a wavelength of ray reflected from the surface; and $S_1$ and $S_2$ are signals generated by detectors 107b1 and 107b2. The diagram 154 shows that the wavelength corresponding to focus point 104a produced the highest value, thereby a location of the surface 109 can be determined by means of the wavelength in question in a way described previously in this document, for example.

Figure 2D:
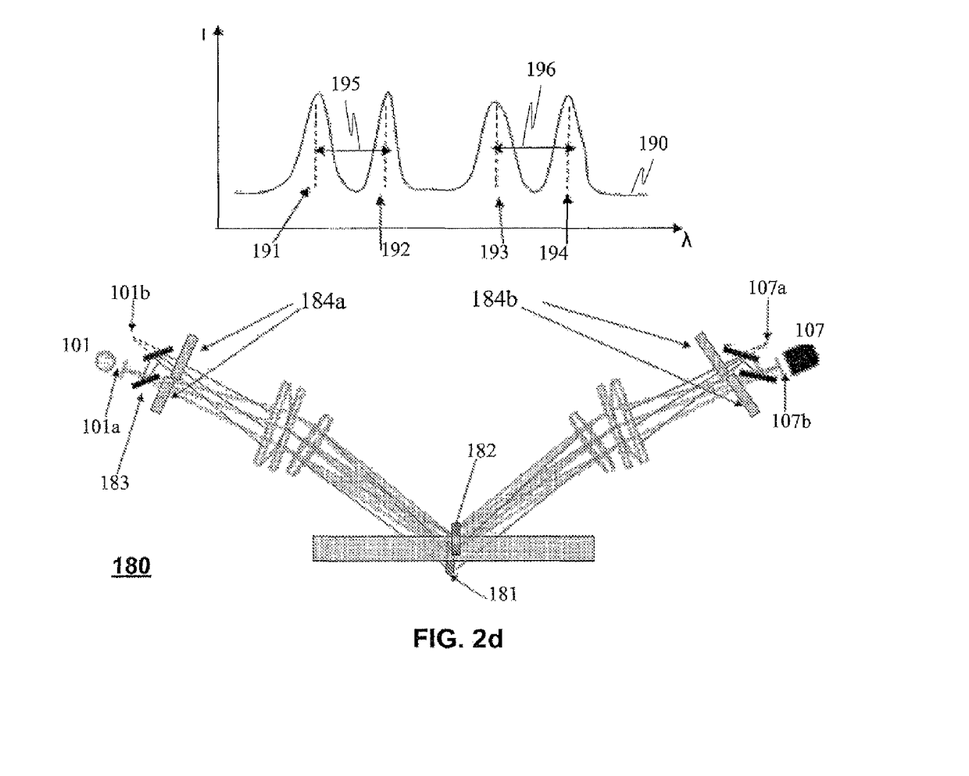
FIG. 2d illustrates the third one of the exemplary measurement device according to an embodiment of the invention.

FIG. 2d illustrates the third exemplary measurement device 180 according to an embodiment of the present invention, wherein an optical radiation source 101 comprises two or more light sources 101a, 101b, both of that form separate spectra 181, 182 to the same surface point, but different heights. Said light sources may be formed by several separate light sources, or be formed e.g. by the radiation from the one optical radiator by means of a beam splitter 183, as shown in FIG. 2d.

In addition, a measurement device 180 of FIG. 2d comprises an optical radiation detection unit 107, which may comprise few separate spectrographs 187a, 187b, for detection of rays emitted by both radiation sources and reflected from the surface of the object being measured, or, alternatively, focused to several different places rays may be combined by the beam splitter to the same detector 107. Radiation detection units 107a, 107b of the measurement device 180 of FIG. 2d are preferably arranged so, that they substantially measure only the intensity of the radiation from so-said own radiation source, regardless of the others. In this case an optical radiation, reflected from the same place on the surface, is received only by that detector, which is in focus at the same wavelength with its own transmitter. Each detector can have e.g. own separate wavelength at which the transmitter is focused on the measured surface, thereby the only one transmitter-receiver pair is in focus with each other at the same wavelength.

It is also possible, that transmitter-receiver pairs have among each other different polarization levels or directions (components 184a, 184b changing the polarization level can be arranged, for example, the way as it is depicted on FIG. 2d), in which case measurement device 180 can be arranged to measure two reflection signals coming from the exactly same place, but which would have different polarization ratio between transmitter and receiver. For example:

transmitter 101a and receiver 107a, wherein the outgoing optical radiation is, e.g., S-polarized and the reception is also S-polarized; and transmitter 101b and receiver 107b, wherein the outgoing optical radiation is, e.g., P-polarized and the reception is also P-polarized;

It is also possible to use variations of another kind, like, for example transmitter 101a and receiver 107a: outgoing optical radiation is S-polarized and the reception is P-polarized (or, for example, circularly polarized, etc.)

By exploiting these various combinations it is possible to measure surface's properties, such as, e.g. thickness, gloss degree and/or refraction index of a film ellipsometrically. In particular it should be noticed, that the measurement device of FIG. 2d is preferably arranged to determine properties of the object's surface in two or more wavelength zones, in which case an output from the detector and detectors is represented by the curve, in accordance with the diagram 190. There two first peaks 191, 192 are caused by the radiation emitted by the first optical source, where peak 191 is a peak from rays reflected from the upper surface of the object, and peak 192 is a peak from rays reflected from the lower surface of the object. Further, two other peaks 193, 194 are caused by the radiation emitted by the second optical source, where peak 193 is a peak from rays reflected from the upper surface of the object, and peak 194 is a peak from rays reflected from the lower surface of the object. This way it is possible to simultaneously determine a height of the interface (upper and lower surfaces) of the object at two different wavelengths and, if needed, also with different polarization. A distance between the surfaces and, accordingly, also a thickness of an object can be determined from the distance between peaks 195, 196.

Figure 3A:
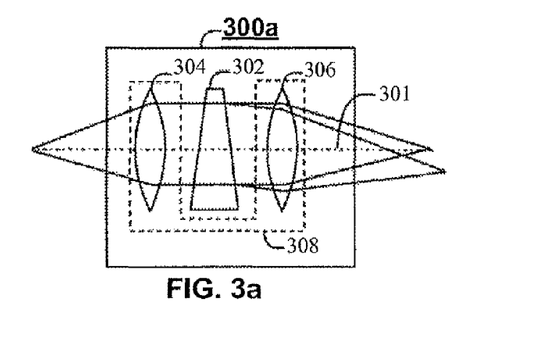
FIG. 3a illustrates an exemplary optical radiation processing unit, according to a certain embodiment of the present invention.

FIG. 3a illustrates an exemplary optical radiation processing unit 300a according to a certain embodiment of the present invention, for focusing various wavelengths of optical radiation coming from the optical source 101 to the measured object in another way. An optical radiation processing unit 300a can comprise a chromatically dispersive component 302, which is adjusted to disperse the optical radiation directed to the measured surface non-axially. In such a way, an optical radiation is dispersed by the dispersive component 302 in a direction deviating from an optical axis 301 of the optical radiation processing unit 300a; thereby a dispersion, or distribution of wavelengths, is at least partly directed to the direction of the normal of the measured surface.

It should, however, be noted; that a focus point direction does not necessarily need to be parallel to the direction of the normal of the surface, but, those directions have a common vector component (i.e. focus points are neither aligned horizontally, nor along the optical axis).

According to the solution of FIG. 3a, a dispersive component 302 is located between two focusing lenses 304, 306. Lenses 304, 306 form a focusing component 308.

A radiation, coming from the optical source in between the lenses can be collimated. The dispersive component 302 together with the focusing component 308 can focus optical radiation of different wavelengths of optical source to different heights in the direction of the normal of the measured surface. As a dispersive component 302 may be a prism or a lattice or, instead of lens or in addition to it, focusing mirrors can be used. Either lenses 304, 306 may be substituted also by lens combination, mirror, mirrors combination or by combination of these.

Figure 3B:
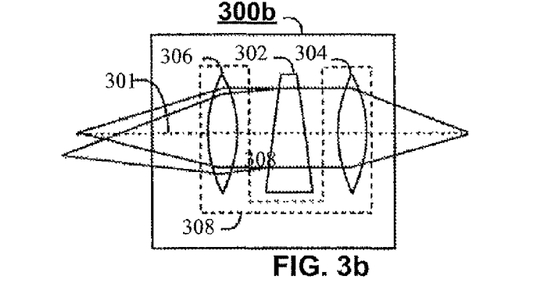
FIG. 3b illustrates the other exemplary optical radiation processing unit, according to a certain embodiment of the present invention.

FIG. 3b illustrates another exemplary optical radiation processing unit 300b, according to an embodiment of the present invention, for focusing optical radiation, reflected from the measured object, to the detector by a focusing component 308, which comprises lenses 304 and 306. In this case, a focus point of an optical radiation processing unit 300b can be on the measured surface or close to it. Without a dispersive component 302 the depth of field will be sufficiently good in a focus point surroundings.

An optical radiation processing unit 300b may also comprise a dispersive component 500 that removes the dispersion and enables merging the wavelengths, travelled by different optical paths, into the same focus. In such a case, focus points located in front of the optical radiation processing unit 300b may be at the same place, to where an optical radiation processing unit 300a focuses different wavelengths (see, e.g. FIG. 3a). In such a case a reflection from the measured surface proceeds intensively. By using a dispersive component 302 scattered apart wavelengths focus behind the optical radiation processing unit 300b to the same focus point, e.g. to the detector, and the detection can be performed by, e.g. a single detector element.

It should be noted, that optical radiation processing units 300a, 300b can be identical, but the intensity values of the lenses, they comprise, and dispersive components can also be different.

Figure 4:
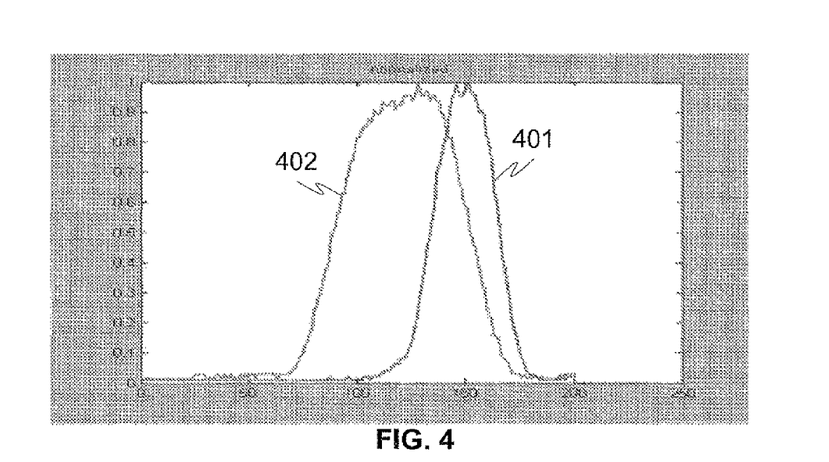
FIG. 4 illustrates two exemplary signals for the thickness measurement of a thin film, according to a certain embodiment of the present invention.

FIG. 4 illustrates two exemplary signals for the thickness measurement of a thin film, according to an embodiment of the present invention, wherein signal 401 represents a characteristic signal width caused by a single wavelength to the measurement device for example during measuring of an optical radiation reflected from a mirror surface. The other signal 402 represents wavelengths widening caused by two different wavelengths, which wavelengths widening thus results from two different optical rays, reflected from the object's upper- and lower surfaces, which have different wavelengths. Thickness of the object (i.e. a distance between its upper- and lower surfaces) can be, according to an embodiment of the invention, determined directly proportional to the Full Width at Half Maximum value of signal 402, as described elsewhere in this document.

Figure 5:
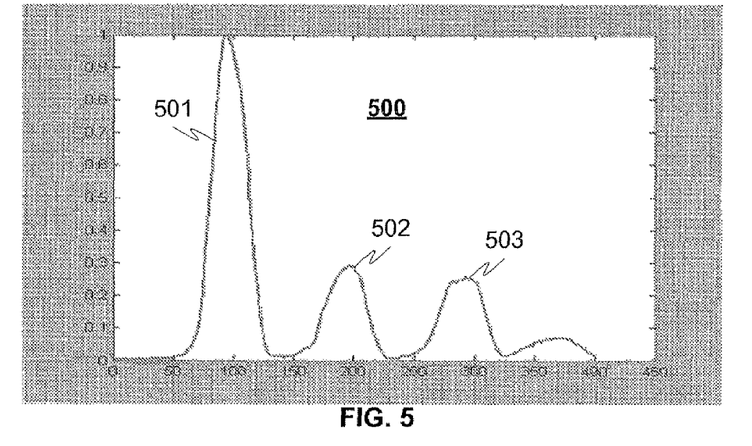
FIG. 5 illustrates an exemplary signal for the thickness measurement of a transparent multilayered structure, according to a certain embodiment of the present invention.

FIG. 5 illustrates an exemplary signal 500 for the thickness measurement of a transparent multilayered structure, according to an embodiment of the present invention. Herein, a distance between layers is such that rays, reflected from any optical interface or at least from the surface in between the layers, are shown as signal peaks 501, 502, 503, in which case a location and/or thickness of layers can be determined in a way, according to the invention, as described elsewhere in this document.

Figure 6A:
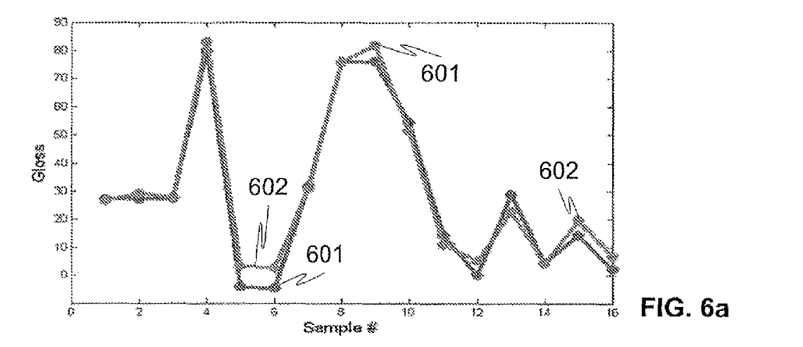
FIG. 6a illustrates the results of a gloss degree measurement carried out by both a measurement device according to the invention and by a commercial instrument.
Figure 6B:
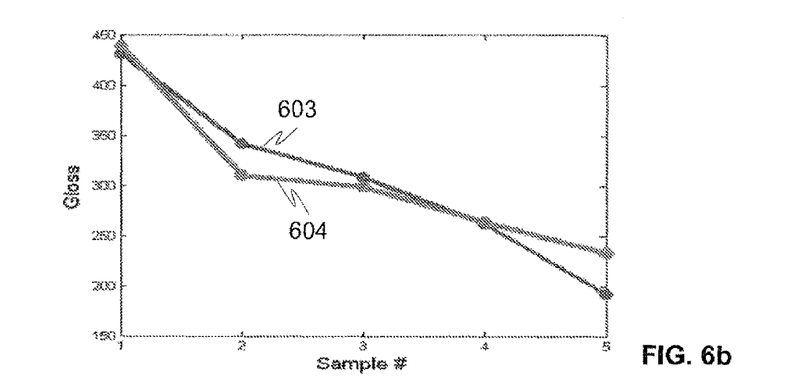
FIG. 6b illustrates the results of another gloss degree measurement carried out by both a measurement device according to the invention and by a commercial instrument.

FIG. 6a illustrates the result of a gloss degree measurement for a painted steel sample carried out by both a measurement device based on chromatic aberration according to the invention (diagram 601) and by a commercial instrument (diagram 602). Moreover, FIG. 6b illustrates the results of the other gloss degree measurement for a stainless steel sample carried out by both a measurement device based on the chromatic aberration according to the invention (diagram 603) and by a commercial instrument (diagram 604). From the diagrams it can be seen that both methods give very similar results.

Represented above are just some of the embodiments of the solution according to the invention. The principles of the invention can be naturally modified within the scope defined by patent claims, for example, for implementation details and operational range.

The invention claimed is:

1. A measurement device for the determination of one or more properties of a measured object, wherein the measurement device comprises:
   at least one optical radiation source for emitting optical radiation to the measured object, and
   at least one detector for receiving radiation reflected from the measured object and for generating an electric signal proportional to an intensity of the reflected radiation,
   characterized in that
   the measurement device in addition comprises
   an emitted optical radiation processing unit, which is adjusted to split the optical radiation emitted by the at least one optical radiation source to separate wavelengths and to direct said separate wavelengths to the measured object in a direction that differs from a normal direction of a surface being measured so that at least a shortest said wavelength and a longest said wavelength of said emitted optical radiation are focused on different depths, in the normal direction of the surface being measured,
   a reflected optical radiation processing unit, which is adjusted to receive the reflected radiation at least in a direction of specular reflection that differs from the normal direction of the surface being measured, and to direct the received optical radiation to said at least one detector,
   wherein the measurement device is adjusted to analyze the electric signal produced by the detector, and to determine at least a characteristic describing a surface property of the measured object, based on an intensity of the wavelength of the emitted radiation, a focus point of which was located on the measured surface, and thus was reflected from that focus point to the detector as a strongest specular geometry wavelength.

2. A measurement device of claim 1, wherein said surface property includes a surface gloss.

3. A measurement device, according to claim 1, wherein:
   the at least one optical radiation source comprises two or more light sources, each said light source generating separate spectra to said surface, but at different said depths, and wherein said light sources are formed either as discrete light sources or by an optical radiator's radiation with a beam splitter, and/or,
   the at least one detector is adjusted to detect rays, reflected from the surface and focused to several different places, said rays being combined by a beam splitter to the detector,
   or wherein the at least one detector comprises two or more detection units that detect rays, that are emitted by each of the at least one radiation source and that are reflected from the surface of the measured object.

4. A measurement device, according to claim 1, wherein
   said at least one optical radiation source comprises two or more light sources, each said light sources generating separate spectra to said surface, but at different said depths, and wherein said light sources are formed either as discrete light sources or by an optical radiator's radiation with a beam splitter, and/or,
   the at least one detector is adjusted to detect rays, reflected from the surface and focused to several different places, said rays being combined by a beam splitter to the detector,
   or wherein the at least one detector comprises two or more detection units that detect rays that are emitted by each of the at least one radiation source and that are reflected from the surface of the measured object, and
   wherein said two or more light sources and the detection units are arranged into transmitter-receiver pairs so that each said detection units is arranged to measure substantially intensities only from a respective radiation source, in which case said transmitter-receiver pairs may have different respective polarization levels or different respective polarization directions, in which case the measurement device can be arranged to measure two or more reflection signals coming from a single place, which reflection signals can have different respective polarization ratios between respective said transmitter and respective said receiver.

5. A measurement device according to claim 1, wherein said surface property is a refraction index and/or a thickness.

6. A measurement device according to claim 1, wherein the measurement device is adjusted to determine a gloss degree $G_0$ that characterizes a gloss of the surface being measured substantially as:

$$G_0 = \frac{G_B - G_A}{\varphi_B - \varphi_A}\varphi_0 + \frac{G_A\varphi_B - G_B\varphi_A}{\varphi_B - \varphi_A}$$

wherein $\varphi_0$ is an intensity measured by the at least one detector; $G_A$ and $G_B$ are respective gloss degrees of first and second references; and $\varphi_A$ and $\varphi_B$ are respective intensity values corresponding to said gloss degrees.

7. A measurement device according to claim 1, wherein a distance to each said wavelength's focus point relative to a reference point is known; and wherein the measurement device is adjusted to define a location of the surface being measured by determining a wavelength of a strongest intensity reflected from the surface being measured and by inferring said location from a distance of the focus point of said wavelength of said strongest reflected intensity from said reference point.

8. A measurement device according to claim 1, wherein the measured object is at least partly transparent to the optical radiation and wherein the object comprises two substantially parallel upper and lower surfaces, and wherein at least the shortest said wavelength and the longest said wavelengths are adjusted to focus so that said surfaces remain in between respective focus points of said shortest and longest wavelengths, and wherein the measurement device is adjusted to receive the wavelengths reflected from the both said surfaces and to determine a thickness of the object based on a peak width change associated with said wavelengths that are reflected from both said surfaces.

9. A measurement device according to claim 1, wherein the measured object is at least partly transparent to the optical radiation and wherein the object comprises two substantially parallel upper and lower surfaces and wherein at least the shortest said wavelength and the longest said wavelength are adjusted to focus so that said surfaces remain in between respective focus points of said shortest and longest wavelengths, and wherein the measurement device is adjusted to determine the wavelengths corresponding to two strongest intensities, and based on the location data of focus points of said wavelengths that correspond to said two strongest intensities, to determine a distance between said upper- and lower surfaces and, therefore, a thickness of the object.

10. A measurement device according to claim 1, wherein a distance to each said wavelength's focus point relative to a reference point is known; and wherein the measurement device is adjusted to define a location of the surface being measured by determining a wavelength of a strongest intensity reflected from the surface being measured and by inferring said location from a distance of the focus point of said wavelength of said strongest intensity from said reference point, and wherein the measurement device is adjusted to determine a profile of the surface being measured when the measured object and the measurement device are moved in relation to each other.

11. A measurement device according to claim 1, wherein a distance to each said wavelength's focus point relative to a reference point is known; and wherein the measurement device is adjusted to define a location of the surface being measured by determining a wavelength of a strongest intensity reflected from the surface being measured and by inferring said location from a distance of the focus point of said wavelength of said strongest intensity from said reference point, and wherein the measurement device comprises two measurement sub-devices, each said sub-device comprising at least one said optical radiation source, one said detector, one said emitted optical radiation processing unit and one said reflected optical radiation processing unit, wherein the first measurement sub-device is arranged to a first half of the object and the second measurement sub-device is arranged to a second half of the object, and wherein the measurement device is adjusted to determine a thickness of the measured object based on location data of a first said surface being measured by the first measurement sub-device and on location data of a second said surface being measured by the second measurement sub-device.

12. A method for determining one or more characteristics of an object by means of optical radiation, comprising:
   emitting the optical radiation by a source of the optical radiation to the object being measured, and
   receiving the radiation, reflected from the object being measured, by a detector, and
   generating an electric signal proportional to the reflected radiation intensity,
characterized in that
additionally in the method
   an optical radiation emitted by the source of the optical radiation is split to various wavelengths that are directed to the measured object in a direction that differs from a normal direction of a measured surface so that at least a shortest said wavelength and a longest said wavelength of said emitted optical radiation are focused on different depths in the normal direction of the surface being measured,
   an optical radiation, reflected from the measured object, is received, at least, from a direction of a specular reflection, that differs from the normal direction of the surface being measured, and said optical radiation is directed to the detector, and
   an electric signal produced by the detector and proportional to the intensity of the radiation focused thereto, is analyzed, and, further, one or more characteristic describing the measured object, based on an intensity of a wavelength, a focus point of which was located on the measured surface and was reflected from that focus point to the detector as a strongest specular geometry wavelength.

13. A computer-readable non-volatile storage medium having embodied thereon computer code for the determining one or more characteristics of a measured object, the computer code comprising program code for receiving measurement data from a measurement device that comprises:
   at least one optical radiation source for emitting optical radiation to the measured object, and
   at least one detector for receiving radiation, reflected from the measured object, and for generating an electric signal proportional to an intensity of the reflected radiation, characterized in that
the measurement device further comprises
- a emitted optical radiation processing unit, which is adjusted to split the optical radiation emitted by the at least one optical radiation source to separate wavelengths and to direct said separate wavelengths to the measured object in a direction that differs from a normal direction of a surface being measured so, that at least a shortest said wavelength and a longest said wavelength of said emitted optical radiation are focused on different depths, in the normal direction of the surface being measured,
- a reflected optical radiation processing unit, which is adjusted to receive the reflected radiation least in a direction of specular reflection that differs from the normal direction of the surface being measured, and to direct the received optical radiation to said at least one detector,
- the computer code further comprising program code for analyzing the electric signal produced by the detector, for determining one or more characteristics describing a surface property of the measured object, based on an intensity of the wavelength of the emitted radiation, a focus point of which was located on the measured surface, and thus, reflected from that focus point to the detector as a strongest specular geometry wavelength.

* * * * *